United States Patent [19]

Gilman

[11] Patent Number: 4,600,001
[45] Date of Patent: Jul. 15, 1986

[54] COMBINED WOUND DRESSING AND DELIVERY MEANS COMPOSITE

[75] Inventor: Thomas Gilman, Palatine, Ill.
[73] Assignee: The Kendall Company, Boston, Mass.
[21] Appl. No.: 641,127
[22] Filed: Aug. 15, 1984
[51] Int. Cl.⁴ ............................................. A61L 15/00
[52] U.S. Cl. ..................................... 128/156; 604/304; 604/307
[58] Field of Search ................ 128/155, 156; 604/304, 604/307, 308

[56] References Cited

U.S. PATENT DOCUMENTS

| | | | |
|---|---|---|---|
| 3,520,306 | 7/1970 | Gardner et al. | 128/156 |
| 3,779,242 | 12/1973 | McCulloch | 128/156 |
| 4,176,664 | 12/1979 | Kalish | 128/156 |
| 4,245,630 | 1/1981 | Lloyd et al. | 128/155 |
| 4,265,234 | 5/1981 | Schaar | 128/156 |
| 4,413,621 | 11/1983 | McCracken et al. | 128/156 |
| 4,513,739 | 4/1985 | Johns | 128/156 |
| 4,526,166 | 7/1985 | Silber | 128/156 |

Primary Examiner—William R. Dixon, Jr.
Assistant Examiner—Steven Capella
Attorney, Agent, or Firm—Alvin Isaacs

[57] ABSTRACT

A wound dressing and delivery means laminate composite is described comprising contiguously oriented and coplanary arranged discrete layers. A centrally-disposed wound dressing layer is in separable and releasable contiguous adhesive contact through an adhesive surface with an adjacent non-adhesive surface of a release liner layer. A non-adhesive surface of the wound dressing layer is further in separable and releasable contiguous heat lamination contact with an adjacent second non-adhesive surface of a delivery means layer. In using, the release liner layer is first peelably separated from the adhesive surface of the centrally disposed wound dressing layer with which it is in releasable adhesive contact. Next, the remaining adherent wound dressing layer and delivery means layer of the wound dressing composite are positioned over the wound application site and applied to said site by contact adhesion. Finally, the delivery means layer is peelably separated from the adjacently contiguous adhering surface of the wound dressing layer.

6 Claims, 14 Drawing Figures

COMBINED WOUND DRESSING AND DELIVERY MEANS COMPOSITE

BACKGROUND OF THE INVENTION

The present invention relates to bandage constructions in general.

This invention also relates to laminated wound closure systems and, more particularly, relates to thin film transparent wound dressing membranes.

The present invention most particularly relates to an improved positioning or delivery system for a polymeric wound dressing membrane to a wound site.

Thin polymeric, or the like, film adhesive dressings represent a relatively new way of managing wounds, differing from traditional absorbent dressings. The advantages of these new non-absorbent wound dressings include reduced patient discomfort, better wound autolysis of necrotic tissue, and faster healing.

A disadvantage of the conventional non-absorbent wound dressings now being used, is that the thin, self-adhesive wound covering membrane is very difficult to handle, and therefore difficult to apply properly to the patient. Another disadvantage of these dressings, is that they can be difficult to remove, and since the membrane is transparent and extremely thin, it can be difficult to locate the edge of the wound dressing and to start its removal from the patient.

The present invention solves the prior art difficulties, and provides a means of making it easier to handle the thin adhesive film wound dressing, and to deliver it to the patient in a precise, convenient way. It also provides for a dressing that has paper tape handles at the perimeter that will both serve to make it easy to find the dressing edge for removal, as well as provide a writing surface for recording important patient medical information.

The novel wound dressing delivery system of the present invention comprises a matte surface thin urethane wound dressing film, supported by a matte surface transparent ethylene vinyl acetate film delivery means layer. It is important that these components have a matte surface, since we have found that a matte non-glare surface is is preferred for aesthetic reasons both by the health care personnel and by the patients. It is also important that the delivery means layer be transparent, so that the wound dressing composite can be positioned properly with the delivery means layer still in place.

When utilizing the present invention, there is no need for the operator to handle the wound application regions of the polymeric wound dressing during the application process. Further, upon separation of the release liner layer from its adherent wound dressing layer adhesive surface, the wound dressing will maintain its semi-rigid, essentially planar configuration prior to the application of the wound dressing and delivery means composite to the wound application site.

The instant invention provides for sterility of the wound dressing layer during application, and wound site contamination will not occur during application of the wound dressing composite. Further, the tape tab removal via perforations insures aseptic conditions adjacent to the wound application site.

SUMMARY OF THE INVENTION

An object of the present invention is to provide a novel wound dressing construction.

Another object of the present invention is to provide an improved positioning or delivery system for the application of a polymeric wound dressing construction to a wound site.

It is yet another object of the present invention to provide a wound dressing and delivery means composite which is at once economical to produce, simple to use, and will maintain its initial sterile conditions during and subsequent to its application to the wound site.

A laminate wound dressing composite structure is provided herein that is designed for dressing either wounds or catheter puncture sites. The layers of the laminate structure arranged from the upper surface to the lower surfaces include: a semi-rigid, non- flexible dressing backing, being a delivery means layer, which has no adhesive on either its top or bottom surface; the intermediate layer in the laminate is preferably a polymeric conformable wound dressing layer which incorporates a pressure-sensitive adhesive on its lower surface; the bottom or undersurface layer is a release liner layer being usually a paper or thermo-plastic layer.

After removal of the entire pre-packaged wound closure laminate from its enclosure, the release liner layer, if present, is peeled away from the pressure-sensitive adhesive of the centrally disposed wound dressing layer. The remaining two adherent layers of the laminate are now pre-positioned over the wound application site, that has been previously prepared and selected for the application of the wound dressing. The semi-rigid combined delivery means layer and its associated wound dressing layer being generally transparent, will permit careful prepositioning of the wound closure layer along with its still adherent delivery means layer.

The generally matte transparent semirigid continuous layer structure of the delivery means layer, also aids in both the wound site visibility characteristics and the maintenance of the modulus of rigidity of the wound dressing composite.

When the wound dressing layer is finally palced in contact with the skin surface, a gentle rubbing across the top surface of the delivery system layer will create a completely smooth wrinkle-free contact between the skin and the polymeric wound closure adhesive surfaces.

The final step in the wound dressing application process, is a peeling away of the delivery means layer from its releasably adherent wound dressing layer, starting at a corner of the delivery means layer, and uncovering the now firmly attached polymeric wound closure layer. The adhered thin, transparent, extremely elastic, polymeric wound closure film is wound sealing, occlusive and waterproof. Although being liquid non-porous, moisture vapor and gases are freely permeable across the wound dressing membrane, allowing the interchange of these gases to aid wound healing, while at the same time protecting the wound site from bacterial contamination.

BRIEF DESCRIPTION OF THE DRAWINGS

In order that the invention may be more readily understood, and so that further features thereof may be appreciated, the invention will now be described by way of example with reference to the accompanying drawings, in which.

DETAILED DESCRIPTION OF THE PREFERRED EMBODIMENT

Figure 1:
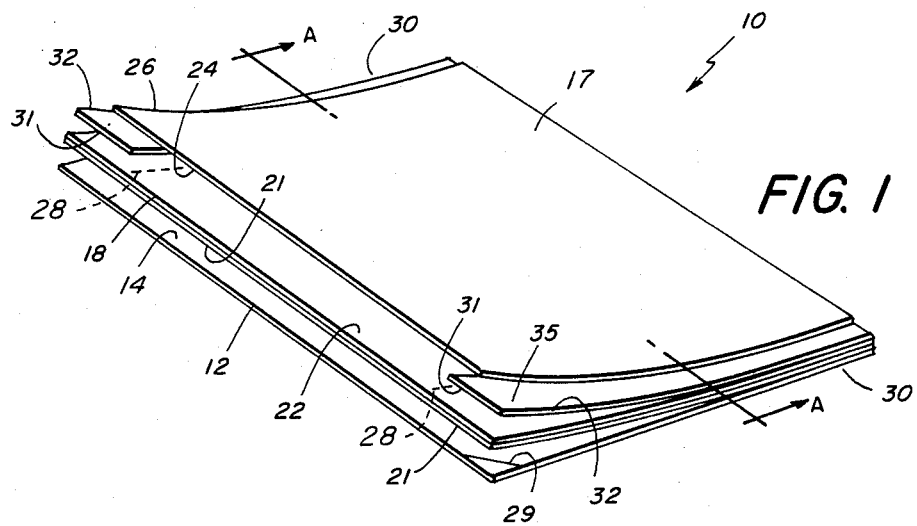
FIG. 1 is a perspective, partially open view, of the wound dressing composite in accordance with the prevent invention.
Figure 2:
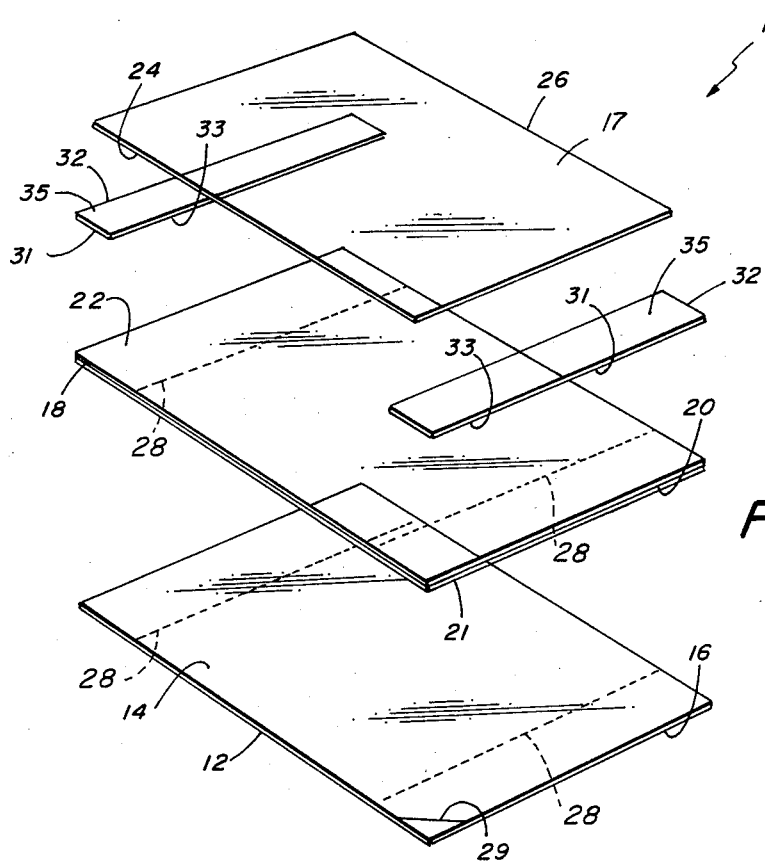
FIG. 2 is an exploded view of the wound dressing composite in accordance with the present invention.
Figure 4:
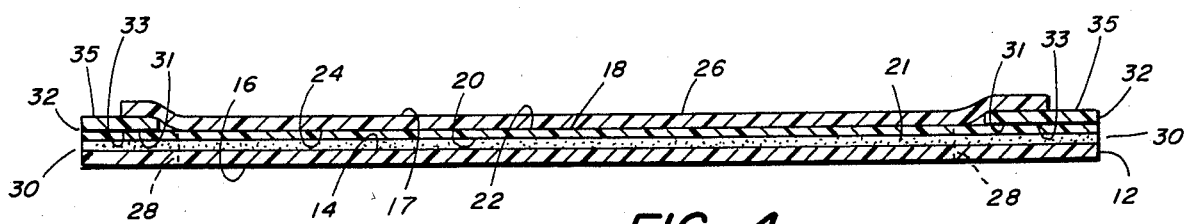
FIG. 4 is a cross-sectional view of the wound dressing composite in accordance with the present invention taken along lines A—A of FIG. 1.
Figure 3A:
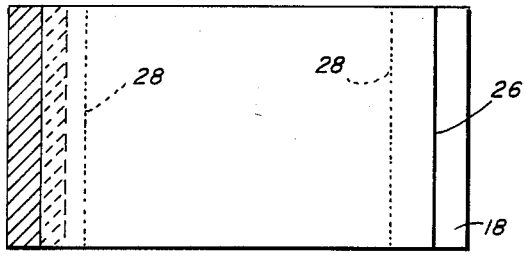
FIGS. 3A–3F are top plan views of the wound dressing composite alternate embodiments of the present invention.
Figure 3D:
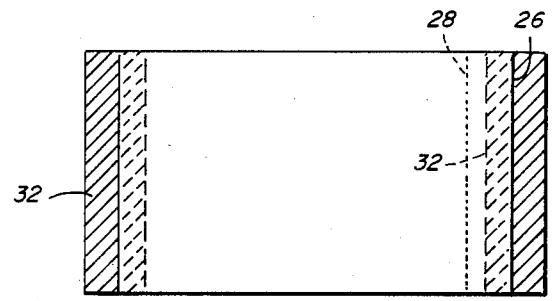
Figure 3B:
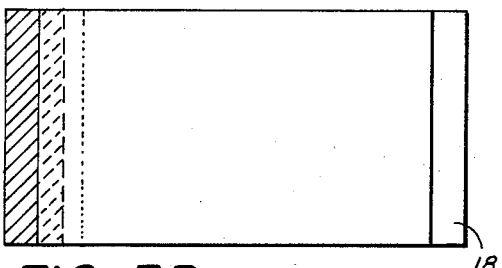
Figure 3E:
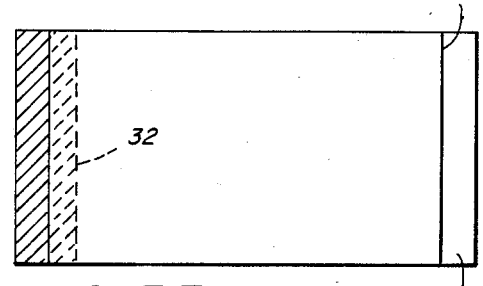
Figure 3C:
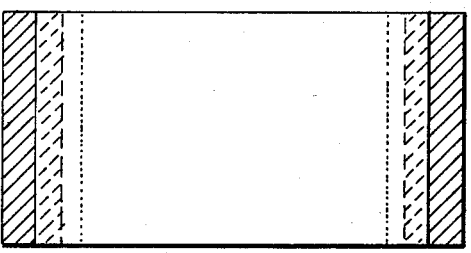
Figure 3F:
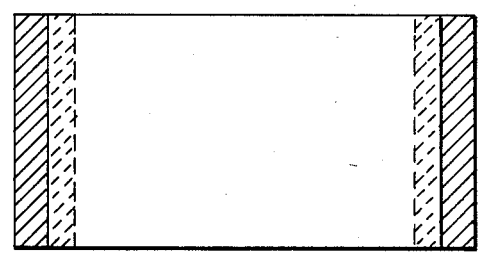

Referring now to FIGS. 1, 2, and 4 of the accompanying drawings, a composite wound dressing and delivery means construction in accordance with the present invention shown is depicted as 10. The wound dressing composite 10 is depicted therein as having a generally rectangular shape, although it should be noted that essentially any desired configuration can be achieved during the construction of the present invention. A release liner layer 12 is shown, and may be referred to here as the wound dressing composite lower outer layer merely for distinguishing purposes. The release liner layer 12 has two major coplanar surfaces. The release liner inner surface 14 is shown as being adjacent to the centrally disposed wound dressing layer adhesive surface 20. The release liner outer surface 16 is seen to be the outermost surface of the wound dressing and delivery means composite 10.

The centrally disposed wound dressing layer 18, which preferably may be a flexible, conformable, polyurethane, or the like polymeric membrane, has two major surfaces. An adhesive lower surface 21, that is in releasable adhesive contact with the release liner inner surface 14, is the wound dressing layer adhesive surface 20. This release liner layer surface 14 is coated with a release coating, such as a silicone release coating, or the like, that allows for the easy separability by peeling, of the release liner layer 12 from the adherent adjacent, centrally-disposed and coplanarly arranged wound dressing layer 18. The wound dressing layer upper surface is depicted here as 22.

This wound dressing layer non-adhesive upper surface 22 is located adjacent to and contiguous with the lower nonadhesive surface 24 of the top-mounted upper situated delivery means layer 26. The wound dressing layer non-adhesive upper surface 22, in the assembly construction, is heat laminated to the lower non-adhesive surface 24 of the top-mounted delivery means layer 26. It should be noted that the tape tab 32, upper surface 35, is not heat laminated or bonded to the lower non-adhesive surface 24 of the delivery means layer 26. This lack of a heat lamination bond to the tape tabs 32, upper surface 35, aids in peelability of the delivery means layers 26. The heat laminated releasably bonded delivery means layer 26 is now easily releasable and peelably separable from the contiguous and adherent wound dressing layer upper surface 22 by means of a gentle peeling movement of the delivery means layer 26.

In a preferred exemplary embodiment of the present invention, the delivery means layer 26, comprises an ethylene vinyl acetate polymeric material, but other polymeric materials are also suitable. The overall structural configuration of the delivery means layer 26 is seen to be that of a continuous substantially transparent sheet-like structure, as depicted in FIG. 1 and in the exploded view of FIG. 2.

The modulus of rigidity of the delivery means layer 26 should be variable within the limits of the modulus of rigidity or coeffecient of elasticity required for the delivery means layer 26 to maintain the adherent wound dressing layer 18 in a relatively rigid and substantially non-flexible planar configuration, following the removal or absence of the release liner layer 12 from the wound dressing composite 10.

Several alternate exemplary embodiments of the wound dressing composite 10 of the present invention are seen in top plan view in FIGS. 3A–3F.

The presence of perforations, depicted here as 28, incorporated in either or both the delivery means layer 26, and the contiguosly-oriented wound dressing layer 18, is shown in several of the alternate exemplary embodiments depicted therein. More detailed specifics concerning the function of the perforations 28 will be described below in the disclosure.

The perforations 28 in selected depicted embodiments of the present invention are arranged in essentially a linear pattern, and are shown as being located in the peripheral, or outer regions of the wound dressing layer 18, and/or the delivery means layer 26, said perforations 28, being oriented substantially parallel to the outer edges 30 of the wound dressing composite 10 of the present invention. The perforations 28 are also positioned slightly central to the tape tab 32 inner border. It is also to be noted that the use of only one row of perforations 28, as shown in FIG. 3, in embodiments 3B and 3D, or two rows of the perforations 28, as in embodiments 3A and 3C, can be employed as desired in various exemplary embodiments.

It is also to be noted that perforations 28, may in selected embodiments be present only in the wound dressing layer 18, and not in the delivery means layer 26 of the wound dressing composite 10 of the present invention.

In relation to the above, further various selected embodiments of the present invention depicted as 3E and 3F, are shown where no rows of perforations 28 are incorporated in either the delivery means layer 26 or the wound dressing layer 18 of the wound dressing composite 10.

The presence of tape tabs 32, mounted on the top surface 22 of, and located in one or both of the outer peripheral regions of the wound dressing layer 18, is also depicted in FIG. 3 in the selected exemplary embodiments shown therein.

These outer edge-oriented tape tabs 32, are essentially elongated, substantially rectangular, parallel-aligned tape tabs 32, that are situated in the peripheral regions of the wound dressing layer 18, and are located adjacent to, but not quite flush with, the outer edges 30 of the wound dressing composite 10, as noted in FIGS. 1 and 3. The tape tabs 32 serve to facilitate handling and separability of the discrete layers of the wound dressing composite 10, as well as serving as a writing surface for the recording of important patient medical information thereon.

As further shown in FIG. 4, a cross-sectional view through the wound dressing composite 10 of the present invention taken through lines A—A of FIG. 1, the wound dressing tape tabs 32, when present in an exemplary embodiment of the present invention, are located along either one or both of the peripheral regions situated parallel and adjacent to, but not quite flush with, the outer edges 30 of the wound dressing layer 18 and the delivery means layer 26.

As noted, the tape tabs 32 are essentially elongated and substantially rectangularly-shaped discretely defined strips comprised of preferably paper tape, or the like, that are applied to either one or both of the outer regions of the top surface 22, of the wound dressing layer 18.

The bottom surface 31 of the tape tab 32 has a pressure-sensitive adhesive layer 33 adhering thereto. This pressure-sensitive adhesive layer 33 adheres the tape tab 32 to the top surface 22 of the wound dressing layer 18.

The wound dressing layer 18, as well as the delivery means layer 26 are preferably matte and transparent for positioning purposes. However, if an opaque wound dressing layer 18, and/or delivery means layer 26, is preferred to be employed, this may also be an alternative exemplary embodiment.

In order to clearly distinguish the tape tabs 32, from the adjacent regions of the wound dressing layer 18, or delivery means layer 26, it may be preferable to employ a tape tab 32 having a distinguishing color.

Referring now to FIG. 5 which is a schematic view of the wound dressing composite 10 and its wound site application procedure, the wound dressing application steps are described below. During use of an exemplary embodiment of the present invention, the wound dressing composite 10, is first removed from an optionally provided conventional protective carrier. View 5A of FIG. 5 shows the release liner layer 12, present in the particular exemplary embodiment, being peelably separated from the releasably adherent, contiguously adjacent, wound dressing layer adhesive surface 20. View 5B shows the now remaining layers of the wound dressing composite, i.e. the wound dressing layer 18 and the contiguously-adjacent, separably adherent, delivery means layer 26, being carefully positioned over the wound application site 40, utilizing the tape tabs 32, and further aided in the locationing by the transparent nature of the still adherently associated wound dressing layer 18 and delivery means layer 26.

As indicated previously in the disclosure, the modulus of rigidity, or the non-elasticity of the delivery means layer 26, aids in maintaining the relatively rigid and planar configuration of the combined wound dressing layer 18 and delivery means layer 26, until the final positioning and adhesion of the wound dressing composite 10 to the wound application site 40. A minimal digitally applied pressure across the top of the non-adhesive surface 17 of the just applied wound dressing delivery means layer 26, at this point, insures adequate skin contact and adhesion of the wound dressing layer 18 without unwanted trapped air pockets or contact wrinkles, or other flaws, at the wound application site 40.

At this point, the topmost delivery means layer 26 is readily separated from the heat laminated adjacent and contiguous non-adhesive surface 22 of the wound dressing layer 18, by lifting a corner set back from edge 32 of the delivery means layer 26, and peeling it away from the underlying adherent wound dressing layer 18 with its still adherent outer aligned tape tabs 32 (see view 5C of FIG. 5).

The delivery means layer 26 is bonded to the wound dressing layer 18 in the area between the tape tabs 32. The bond is achieved by a thermal lamination process as described. This process does not bond the delivery means to the layer tape tabs 32 only to the wound dressing layer 18. The unbonded portions of the sheet that overlap the tape handles then provide convenient tabs to grasp for peeling the support sheet from the dressing.

In the exemplary embodiments discussed above which incorporate rows of perforations 28 within the wound dressing layer 18 and/or the delivery means layer 26, the final step in the process of wound dressing application is the removal of the peripheral regions of the perforated wound dressing layer 18, and/or the delivery means layer 26, if desired, by peeling the tape tab regions away from the remaining adhered wound dressing layer 18 (see view 5D of FIG. 5). The entire wound dressing composite skin application process is now complete and a sterile physically intact protective wound dressing is conformably affixed to the wound application site 40.

To summarize, the delivery system, functions in the following way: first, the release liner layer 12 is peeled away from the wound dressing layer 18. The peel is started by "cracking" the release liner layer 12 at the corner notch 29 that is cut almost all the way through to the wound dressing layer 18. The wound dressing layer 18 which is supported by the heat laminated adherent delivery means layer 26, is now delivered to the wound application site 40 and positioned as desired. It is then pressed to the skin surface to get a satisfactory pressure-sensitive adhesive bond to the skin. The delivery means layer 26 is now peeled off and discarded, leaving the wound dressing layer 18 in place. The paper tape tab strips 32 can be left in place to aid in later wound dressing layer removal 18, or they may be removed by tearing at the perforation line 28. Alternatively, the tape tabs 32 can be removed and repositioned with recorded patient data.

The peel strength of the bond between the heat laminated delivery means layer 26 and the wound dressing layer 18 must be within a critical range for the present invention to function properly. If the heat laminated bond is too weak, the delivery means layer 26 will be separated when the release paper layer 12 is peeled off. If the heat laminated bond is too strong, the dressing layer 18 will be dislodged from the patient when the delivery means layer 26 is peeled away from the adherent wound dressing layer 26.

A proper bond has been achieved by the use of an ethylene vinyl acetate delivery means layer 26 that is thermally bonded to a urethane wound dressing layer 26. In order for this method of achieving a peelable heat laminated bond to be successful, the polyurethane wound dressing layer 18 should have a matte, or rough, surface.

Figure 6:
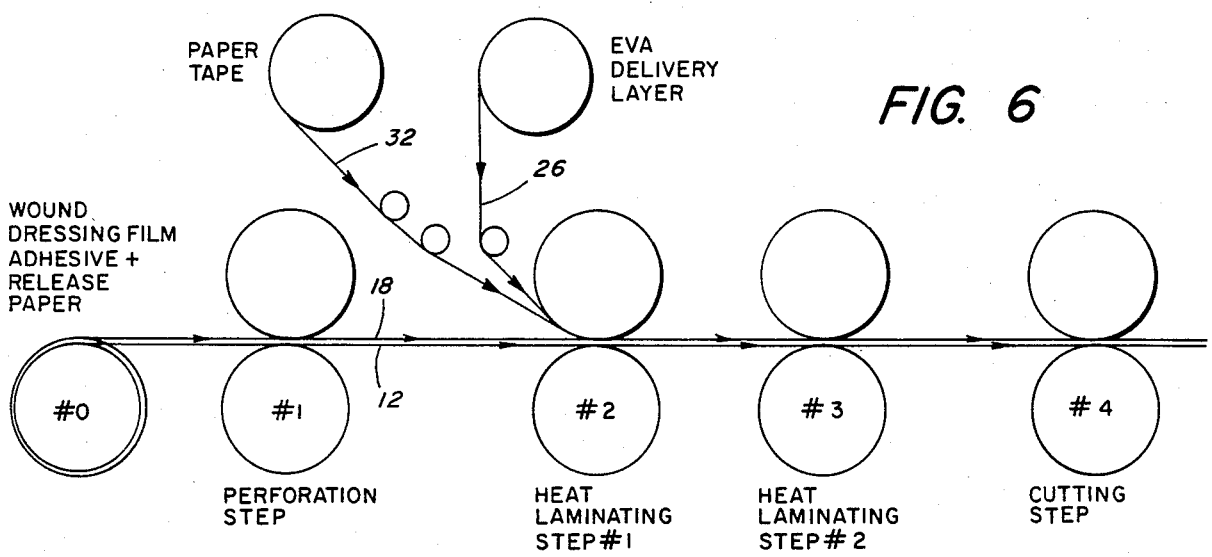
FIG. 6 is a schematic view of the method of assembly of the wound dressing composite of the present invention.
Figure 5A:
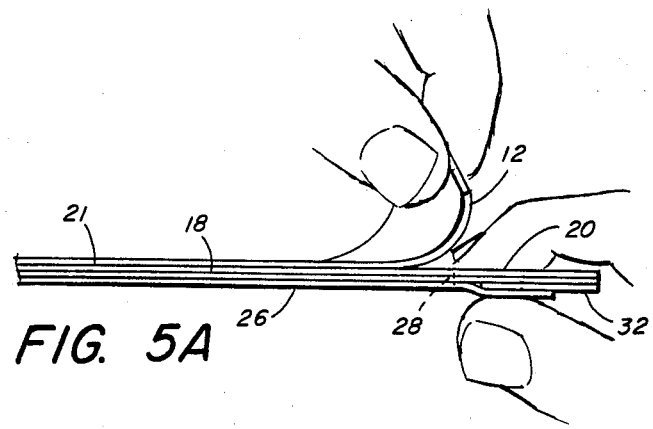
FIGS. 5A–5D are schematic views of several operational stages in the application of the present invention to a wound application site.
Figure 5B:
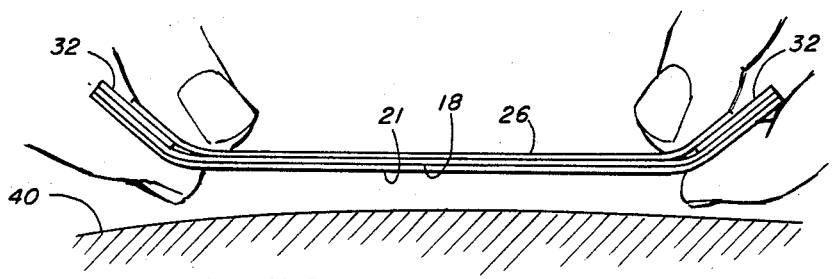
Figure 5C:
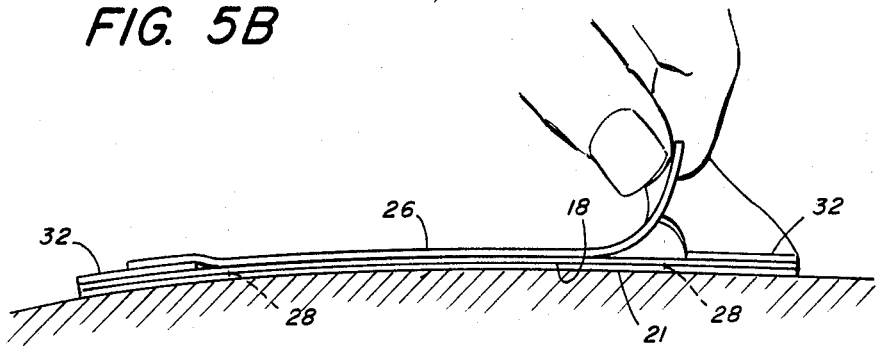
Figure 5D:
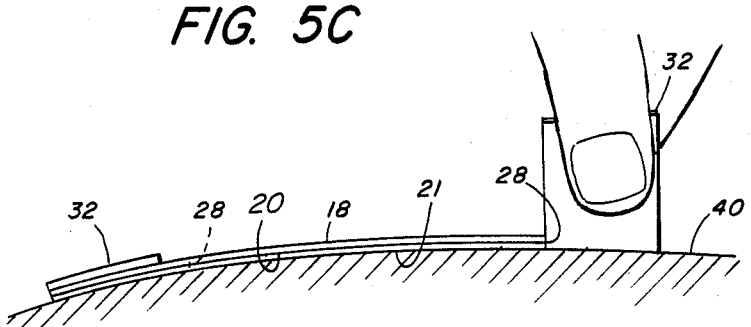

FIG. 6 is a schematic view of the method of assembly of the wound dressing composite of the present invention.

The method of construction of the wound dressing composite 10 is illustrated in FIG. 6. A roll #0 containing the delivery means layer 26, the wound dressing layer 18, and the tape tabs 32 is made by conventional coating and laminating techniques, slit to desired width, and fed to the beginning of the converting line. At roller #1, the perforations 28 contiguous to the paper tape tabs 32 are cut, as well as the corner notch 29 for aid in the release liner layer 12, starting the release peel. The paper tape and ethylene vinyl acetate delivery means layer 26 material are fed (as rolls) before roller #2. The next two roller stations, #2 and #3, are the heat lamination stations. At the final station (i.e. #4), the dressings are cut to the proper length.

The strength of the peelable heat lamination bond between the ethylene vinyl acetate delivery means layer 26 and the urethane film wound dressing layer 18 depends on the following variables: fabrication line speed, temperature and pressure at the first roller station, as well as the temperature and pressure at the second roller station. A suitable heat lamination bond can be obtained with one heat lamination station, but the control over the resultant heat lamination bond is not as reliable in such a manufacturing process.

By proper choice of the above-desired process variables, one can achieve a peelable heat lamination bond that is strong enough to hold during delivery of the wound dressing, yet weak enough to allow one to peel delivery means layer 26 from the wound dressing layer 18 without disturbing the dressing.

The mechanism of this heat lamination bond formation has not been fully established. However, it appears to involve the melting of the ethylene vinyl acetate delivery means layer 26, at the interface of the delivery means layer 26 lower surface 24 and the urethane wound dressing layer 18 upper surface 22. The outer surface of the delivery means layer 26 does not melt, however, as the embossing pattern that results in the matte surface remains undisturbed.

The foregoing detailed description of the preferred embodiments of the present invention is given for purposes of clarity of understanding only, and no unnecessary limitations should be understood or implied therefrom, as modifications may be obvious to those skilled in the art.

EXAMPLE

A 4.2 mil sheet of ethylene vinyl acetate was used as the delivery means layer 26. The vinyl acetate content was about 5 percent by weight. The sheet incorporated a microembossing on one side to give a matte appearance.

The polyurethane film comprising the wound dressing layer 18 was solution cast onto a matte paper. This film was then laminated to a layer of pressure-sensitive adhesive that was carried on a silicone coated release paper. The lamination was such that the adhesive was in contact with the smooth, i.e. non-matte, side of the film.

This composite was then heat laminated to the ethylene vinyl acetate delivery means layer 26 under the following conditions: line speed was 18 feet per minute; first hot station temperature was 320° F., pressure was 80 psi; second hot station temperature was 275° F., pressure was 20 psi.

Wound dressing composites 10 prepared in this way were individually packaged and ethylene oxide sterilized. It was found that the peel strength of the heat lamination bond between the wound dressing layer 18 and the delivery means layer 26 decreased and then increased with time. First, the minimal trend toward lower peel strengths was complete two weeks after manufacture, at which time the peel strength then began increasing. This increase in peel strength was slow enough so that dressings aged under accelerated conditions of 120° F. for three months remained fully functional. Additionally, dressings that were aged one year at room temperature have remained functional.

What is claimed is:

1. A wound dressing and delivery system composite comprising:
   a wound dressing layer;
   said wound dressing layer having both an adhesive-coated surface and a non-adhesive coated surface disposed on the opposite thereof; and at least one paper tape tab adhered to a peripheral region of said non-adhesive-coated surface of said wound dressing along a margin thereof;
   a release liner layer;
   said release liner layer being oriented coplanarly adjacent to and releasably secured to said wound dressing layer adhesive surface;
   a delivery means for delivering said wound dressing layer to a wound application site;
   said delivery means having a first non-adhesive-coated surface and a second non-adhesive-coated surface disposed on the opposite side thereof; said delivery means being coextensive in area with said wound dressing layer; and
   said wound dressing layer being centrally disposed between said release liner layer and said delivery means, and further oriented coplanarly adjacent to and releasably secured by means of a heat lamination bond to said second non-adhesive surface of said delivery means layer except in the peripheral region covered by said paper tape tab, said release liner layer being free from heat lamination bond to said paper tab.

2. The wound dressing and delivery system composite as described in claim 1, wherein said wound dressing layer peripheral region incorporates at least one row of perforations.

3. The wound dressing and delivery system composite as described in claim 1, wherein the wound dressing layer comprises a polyurethane, or the like, polymeric membrane.

4. The wound dressing and delivery system composite as described in claim 3, wherein said polymeric membrane is permeable to gases and water vapor.

5. The wound dressing and delivery system composite of claim 1, wherein said wound dressing layer and said delivery means are substantially transparent.

6. The wound dressing and delivery system in claim 1, wherein said wound dressing layer and said delivery means have matte surfaces.

* * * * *